US00PP22517P2

(12) United States Plant Patent
Morgan

(10) Patent No.: US PP22,517 P2
(45) Date of Patent: Feb. 21, 2012

(54) ***BEGONIA* PLANT NAMED 'NZCTHREE'**

(50) Latin Name: *Begonia boliviensis*
Varietal Denomination: Nzcthree

(75) Inventor: Ed Morgan, Auckland (NZ)

(73) Assignee: The New Zealand Institute for Plant and Food Research Ltd (NZ)

( * ) Notice: Subject to any disclaimer, the term of this patent is extended or adjusted under 35 U.S.C. 154(b) by 38 days.

(21) Appl. No.: 12/658,095

(22) Filed: Feb. 1, 2010

(51) Int. Cl.
*A01H 5/00* (2006.01)

(52) U.S. Cl. ..... Plt./343

(58) Field of Classification Search ..... Plt./343, Plt./344, 349
See application file for complete search history.

*Primary Examiner* — Kent L Bell

(57) ABSTRACT

A new and distinct *Begonia* cultivar named 'Nzcthree' is disclosed, characterized by its unique scarlet red flower color and unique foliage. The new cultivar is a *Begonia*, typically suited for garden and ornamental container use.

1 Drawing Sheet

Figure 1:
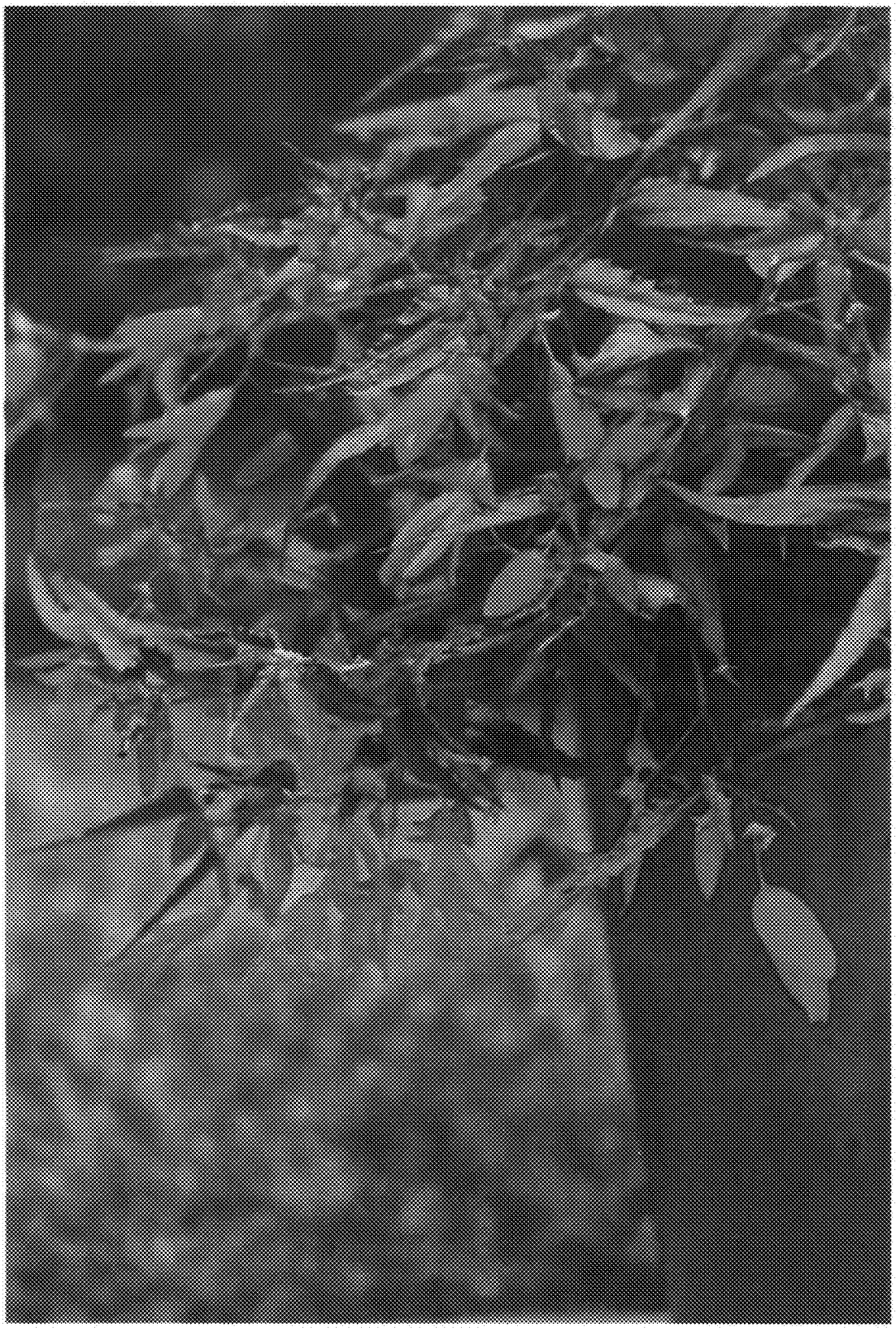

Latin name of the genus and species: *Begonia boliviensis*.
Variety denomination: 'Nzcthree'.

BACKGROUND OF THE INVENTION

The new cultivar is a product of a planned breeding program. The new variety originated from a cross pollination of the seed parent, an unpatented, undistributed proprietary variety of *Begonia boliviensis* known as '02/03 #1' with the pollen parent, an unpatented proprietary selection of *Begonia boliviensis* referred to as 'Dwarf *Boliviensis*' directed by the inventor in February of 2007. The crossing was made in Palmerston North, New Zealand, at a commercial greenhouse.

'Nzcthree' was discovered by the inventor, Ed Morgan in December 2007 in Palmerston, New Zealand at a commercial greenhouse among seedlings resulting from the February 2007 crossing.

After selection of the new cultivar, asexual reproduction of the new cultivar 'Nzcthree' was first performed in the same commercial greenhouse by vegetative cuttings. 'Nzcthree' has since produced several generations and has shown that the unique features of this cultivar are stable and reproduced true to type.

SUMMARY OF THE INVENTION

The cultivar 'Nzcthree' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Nzcthree'. These characteristics in combination distinguish 'Nzcthree' as a new and distinct *Begonia* cultivar:

1. Unique scarlet colored blooms.
2. Distinctive flower shape.
3. Distinctive leaf shape and color.
4. Flattened leaf plane from the stem.

PARENTAL COMPARISON

Plants of the new cultivar 'Nzcthree' are similar to the female parent '02/03#1' in most horticultural characteristics. However, 'Nzcthree' differs in producing darker foliage and different colored flowers.

Plants of the new cultivar 'Nzcthree' are similar to the male parent 'Dwarf *boliviensis*' in most horticultural characteristics. However, 'Nzcthree' differs in producing a flower of a darker color.

COMMERCIAL COMPARISON

Plants of the new cultivar 'Nzcthree' are similar to the patented commercial variety 'Bonfire' U.S. Plant Pat. No. 15,108 in most horticultural characteristics. However, 'Nzcthree' differs in producing plants with larger foliage of different coloration. Additionally, the new variety produces flowers of a solid red color near RHS Red 41A, while 'Bonfire' produces flowers having a variety or orange tones.

BRIEF DESCRIPTION OF THE PHOTOGRAPH

The accompanying photograph in FIG. 1 illustrates in full color a typical flowers, stems and foliage of 'Nzcthree' grown in a greenhouse in Palmerston North, New Zealand. This plant is approximately 3 years old, shown in a 10 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Nzcthree' plants grown in a greenhouse in Palmerston North, New Zealand. Temperatures ranged from 10° C. to 20° C. at night to 12° C. to 25° C. during the day. No artificial light, photoperiodic treatments or chemical treatments were given to the plants. Measurements and numerical values represent averages of typical plant types.

Botanical classification: *Begonia boliviensis* 'Nzcthree'
Age of the plant described: Approximately 3 years.
Container size of the plant described: 10 liter commercial container.

PROPAGATION

Typically reproduced by vegetative cuttings.

Roots: Irregular-shaped tuber. Approximately average 6 cm long by 2 cm in diameter. Tuber colored near Yellow-Orange RHS 22D.

PLANT

Growth habit: Semi-erect. Basal shoots arising vertically, becoming pendulous.
Mature height: Approximately 45 cm.
Plant spread: Approximately 87 cm.
Growth rate: Moderate.
Branching characteristics: Basal branching.
Internode length: Average 3.5 cm.
Stem diameter: Approximately 1.6 cm.
Stem texture: Smooth.
Stem length: Average 60 cm.

FOLIAGE

Leaf:
*Arrangement.*—Alternate and opposite occurring leaves occurring at 90 degree angle from stem.
*Quantity.*—Average between 9 to 15 per branch.
*Average length.*—2.0 cm.
*Average width.*—1.2 cm.
*Shape of blade.*—Curved, non-symmetrical lanceolate.
*Apex.*—Acute.
*Base.*—Oblique.
*Margin.*—Double serrate.
*Texture upper and lower surface.*—Slightly pubescent.
*Aspect.*—Convex curve.
*Color.*—Young foliage upper side: RHS Green 144A. Young foliage under side: RHS Green 144A, and Red 42A from venation. Mature foliage upper side: RHS Green 144A. Mature foliage under side: RHS Green 144C.
*Venation.*—Type: Pinnate. Venation color upper side: RHS Green 144A. Venation color under side: RHS Red 42A.
*Petiole.*—Length: Approximately 1 cm. Diameter: Approximately 0.1 cm. Color: Near RHS Red 42A. Texture: Smooth.

FLOWER

Natural bloom season: Spring until Fall.
Flower arrangement: Singly occurring.
Flower longevity: Approximately 7 to 10 days on plant
Bud:
*Shape.*—Lanceolate.
*Length.*—Approximately 1 cm.
*Diameter.*—Approximately 0.2 cm.
*Color.*—Near RHS Orange-Red 34A.
Flower size:
*Length.*—Average 4.1 cm.
*Depth.*—Average 1 cm.
Tepals:
*Quantity.*—4 or 5.
*Length.*—Approximately 3.5 cm.
*Width.*—Approximately 0.7 cm.
*Shape.*—Overlap at base for approx 10 mm then petals fan out to form a bell shape with gradual out-curving of tips.
*Apex.*—Acute.
*Base.*—Obtuse.
*Margin.*—Entire.
*Texture, upper and lower surfaces.*—Smooth.
*Color.*—When opening, upper surface: Near RHS Red 41A. When opening, lower surface: Near RHS Red 41A. Fully opened, upper surface: Near RHS Red 41A. Fully opened, lower surface: Near RHS Red 41A.
Sepals: Not Present.
Pedicels:
*Length.*—Approximately 3.0 cm.
*Diameter.*—Approximately 0.3 cm.
*Angle.*—About 45° to the lateral branch.
*Texture.*—Smooth.
*Color.*—Near RHS Red 41A.
Bracts:
*Length.*—Approximately 1.8 cm.
*Width.*—Approximately 0.3 cm.
*Quantity.*—2.
*Shape.*—About 70° to the lateral branch.
*Aspect.*—Concave.
*Texture.*—Smooth.
*Color.*—Near RHS Red 41A, upper and lower surfaces.
Peduncles:
*Length.*—Approximately 6 cm.
*Diameter.*—Approximately 0.4 cm.
*Angle.*—About 70° to the lateral branch.
*Texture.*—Smooth.
*Color.*—Near RHS Red 41A.
Stipules: Not observed to date.
Fragrance: None.

REPRODUCTIVE ORGANS

Stamens:
*Number.*—20 to 30.
*Stamen length.*—Approximately 0.25 cm.
*Filament color.*—Near RHS Yellow 10B.
*Anther color.*—Near RHS Yellow 16C.
*Anther shape.*—Linear.
*Pollen.*—Not observed.
Pistil: 3 present
*Pistil color.*—Near RHS red 41A.
*Pistil length.*—Approximately 1 cm.

OTHER CHARACTERISTICS

Seeds: Typical dust-like *Begonia boliviensis* seeds.
Disease/pest resistance: Moderate resistance and susceptibility to common diseases and pests of *Begonia* have been observed in the new variety.
Temperature tolerance: Tolerates temperatures from approximately 4° C. to 38° C.

What is claimed is:

1. A new and distinct cultivar of *Begonia boliviensis* plant named 'Nzcthree' as herein illustrated and described.

* * * * *